(12) United States Patent
Hartley et al.

(10) Patent No.: US 6,524,335 B1
(45) Date of Patent: Feb. 25, 2003

(54) ENDOLUMINAL AORTIC STENTS

(75) Inventors: David Ernest Hartley, Subiaco (AU); Thomas Francis Browne, Essex (GB)

(73) Assignee: William A. Cook Australia Pty. Ltd., Queensland (AU)

(*) Notice: Subject to any disclaimer, the term of this patent is extended or adjusted under 35 U.S.C. 154(b) by 0 days.

(21) Appl. No.: 09/581,671
(22) PCT Filed: Dec. 9, 1998
(86) PCT No.: PCT/AU98/01019
§ 371 (c)(1), (2), (4) Date: Sep. 11, 2000
(87) PCT Pub. No.: WO99/29262
PCT Pub. Date: Jun. 17, 1999

(30) Foreign Application Priority Data

Dec. 10, 1997 (AU) .............................................. PP0835

(51) Int. Cl.[7] .................................................. A61F 2/06
(52) U.S. Cl. ...................... 623/1.13; 623/1.12; 623/1.34
(58) Field of Search ............................... 623/1.13, 1.14, 623/1.15, 1.34, 903

(56) References Cited

U.S. PATENT DOCUMENTS

| | | | |
|---|---|---|---|
| 5,425,765 A | * | 6/1995 | Tiefenbrun et al. ........... 623/12 |
| 5,617,878 A | | 4/1997 | Taheri |
| 5,984,955 A | * | 11/1999 | Wisselink ................... 623/1.13 |
| 6,030,414 A | * | 2/2000 | Taheri ............................ 623/1 |
| 6,077,296 A | * | 6/2000 | Shokoohi et al. ............... 623/1 |
| 6,325,826 B1 | * | 12/2001 | Vardi et al. ................. 623/1.35 |
| 6,395,018 B1 | * | 5/2002 | Castaneda ................... 623/1.13 |

FOREIGN PATENT DOCUMENTS

| | | | |
|---|---|---|---|
| WO | 9516406 | 6/1995 | |
| WO | 9745073 | 12/1997 | |
| WO | 9836709 | 8/1998 | |
| WO | WO 98/53761 | * 12/1998 | ............. A61F/2/06 |

* cited by examiner

Primary Examiner—David H. Willse
Assistant Examiner—Javier G. Blanco
(74) Attorney, Agent, or Firm—Richard J. Godlewski

(57) ABSTRACT

A prosthesis (18) comprising stents (7,8) sutured to a graft (5) comprising a tube of biocompatible material. The stents are attached to the inside surface of the tube and there is at least one fenestration (10) in the tube corresponding to an intersecting artery opening. A further stent (1) extends proximally and may have caudally facing barbs (2). Each fenestration includes one or more radiopaque markers (11) defining a periphery of the fenestration. A release mechanism for the prosthesis includes trigger wires (15,17) stitched into a fold (16) on the material to retain the prosthesis in a partially compressed state during deployment. A delivery device (20) has a sheath (26) to hold the compressed prosthesis during insertion and a top cap (24) to retain the top stent (1).

18 Claims, 8 Drawing Sheets

ENDOLUMINAL AORTIC STENTS

INTRODUCTION

The present invention relates generally to the field of the treatment of aortic disease and in particular to endoluminal aortic stents and a method of deployment of such stents which allows accurate placement of a covered stent in the aorta. In particular it is capable of being deployed and positioned accurately above the renal arteries in the treatment of infra-renal aortic aneurysmal disease.

BACKGROUND OF THE INVENTION

According to the prior art, aortic disease is often treated by surgical techniques involving the use of stents and grafts. For example, it is well known in the art to interpose, within the stenotic portion of an artery, a stent, whether made of stainless steel or other materials, capable of being balloon-expandable for strengthening the walls of a stenotic or occluded artery. In addition, it is well known in the prior art to use a graft to repair highly damaged portions of, for example, the aorta or other arteries thereby ensuring blood flow and reducing the risk of aneurysms or ruptures. The grafts, hollow tubes comprised of material such as dacron, are normally inserted within the walls of a damaged artery and can be sewn into position or expanded through the use of a stented balloon catheter.

A more severe problem occurs when it is necessary to use a graft at or around the intersection of a major artery (e.g. the aorta) with intersecting arteries (e.g. the renal arteries, carotid or brachycephalic artery). While the graft is clearly required to strengthen and ensure the flow of blood through, for example, the aorta, the use of a graft effectively seals or blocks off the blood flow to the kidneys or cerebral circulation. Accordingly, it is often impossible or impractical to use a graft to treat aortic disease at or around the intersection of the aorta and other arteries. Instead a surgeon must attempt to repair the weakened walls of such artery using other surgical techniques having high failure rates and limited success. For example, although several centers around the world have been routinely deploying endoluminal grafts for the treatment of infra-renal aortic aneurisms, as many as 30% of abdominal aortic aneurysms are unsuitable for this method of treatment due to an insufficient length of aneurysmal-free infra-renal aorta to firmly anchor the graft or stent.

The present invention solves the problem in the prior art by utilizing the supra-renal aorta to provide adequate anchorage for an aortic graft whilst at the same time employing extremely accurate placement of a fenestrated covered stent which corresponds to the exact sites of origin of the intersecting arteries.

BRIEF DESCRIPTION OF THE INVENTION

The present invention in general relates to a fenestrated endoluminal aortic stent which is a single component device comprising two or more stainless steel or nitinol stents such as Z stents which may have caudally facing barbs sutured to a variable length of a bio-compatible material tube in which the stents are attached to the inside surface of the bio-compatible material tube and, depending on the geometry of the intersecting arteries to be covered, customized fenestrations accurately placed in the bio-compatible material tube corresponding to the intersecting artery openings.

In one form, therefore, the invention may be said to reside in a prosthesis comprising two or more stents sutured to a graft comprising a bio-compatible material tube, wherein the two or more stents are attached to the inside surface of the bio-compatible material tube and at least one fenestration in the bio-compatible material tube corresponding to an intersecting artery opening.

Preferably there are more than two stents attached to the bio-compatible material tube.

There may be a further stent fastened to the bio-compatible material tube and extending proximally from the bio-compatible material tube.

At least one of the stents may have caudally facing barbs thereon to assist with accurate retention of the prosthesis when completely inserted.

The proximally extending stent may be the stent which has the caudally facing barbs thereon.

The bio-compatible material tube may in one embodiment be a DACRON material tube.

There may be two or more fenestrations according to the number of intersecting arteries.

The or each fenestration may include one or more radio-paque markers defining a periphery of the fenestration.

The distal most of the stents may include a loop extending distally of the graft.

The prosthesis may further include a release mechanism for the prosthesis including one or more trigger wires wherein a portion of the bio-compatible material tube is folded longitudinally with the one or more trigger wires respectively threaded longitudinally through the bio-compatible material tube at the fold to retain the prosthesis in a partially compressed state.

At least one of the stents may include one or more shortened loops to enable location of the fenestrations as required.

Accurate siting of the branches of the aorta may be achieved from Computerised Axial Tomograms (CT) and angiography and the invention is customised to each patient in relation to the sites corresponding with the CT. The fenestrations are marked with radiopaque beads to facilitate their positioning under X-ray control before deployment.

In an alternative form the invention may be said to reside in a method for treating arterial disease at an intersection of two arteries, including the steps of:

X-raying arteries to be treated so as to accurately determine the position of the intersection of the arteries, customizing one or more fenestrations to a prosthesis comprising a selected length of a bio-compatible material tube, attaching radiopaque markers around the or each fenestrations, placing two or more stents into the bio-compatible material tube, bends in the stents being shortened if necessary in such a way so as not to cover the fenestrations, manually gathering a top stent, covering the top stent with a top cap and holding the stent in place in the top cap with a trigger wire, stitching the trigger wire or another trigger wire through a longitudinal fold in the bio-compatible material tube to narrow the diameter of said prosthesis thereby providing a customised fenestrated covered graft to be inserted into an artery to be treated.

The method may further include the step of sewing a further stent to the top ring of the bio-compatible material tube, such that the further stent extends proximally from the bio-compatible material tube.

There may be more than two stents attached to the bio-compatible material tube and two or more than two fenestrations according to the number of intersecting arteries.

The process of insertion of the graft may include the steps of; compressing the graft and placing it into a sheath which fits snugly around the top cap, the prosthesis, the stents and an obturator, inserting through a femoral artery in a groin the prosthesis using a delivery device which includes the top cap, the sheath, the obturator and guide wires, withdrawing the sheath to reveal the graft in semi-deployed position, positioning the prosthesis, partially withdrawing the sheath and obturator to enable insertion of angiography catheters and guide wires, inserting the angiography catheters and guide wires through a contralateral groin into the artery to be treated to provide maneuverability, and accurate positioning of the graft by positioning right and left angiography catheters and guide wires through the fenestrations into the intersecting arteries, releasing the trigger wire to provide full deployment of the the graft, withdrawing said angiography catheters and pushing up the sheath and obturator through the stent and docking with the top cap and fully withdrawing the delivery device, whereby the said fully deployed stent ensures the flow of blood at the intersection of the arteries to be treated.

The method by which the prosthesis of the present invention may be maneuvered into place prior to full deployment is by way of the right and left angiography catheters and guide wires.

The radiopaque markers may be gold or any other bio-compatible material which enables the marker to be visualized by X-ray or other methods.

This generally describes the invention but to assist with understanding of the invention reference will now be made to preferred embodiments of the invention with the assistance of the following drawings.

BRIEF DESCRIPTION OF THE DRAWINGS

One embodiment of the present invention will now be described with reference to the drawings in which.

Figure 1:
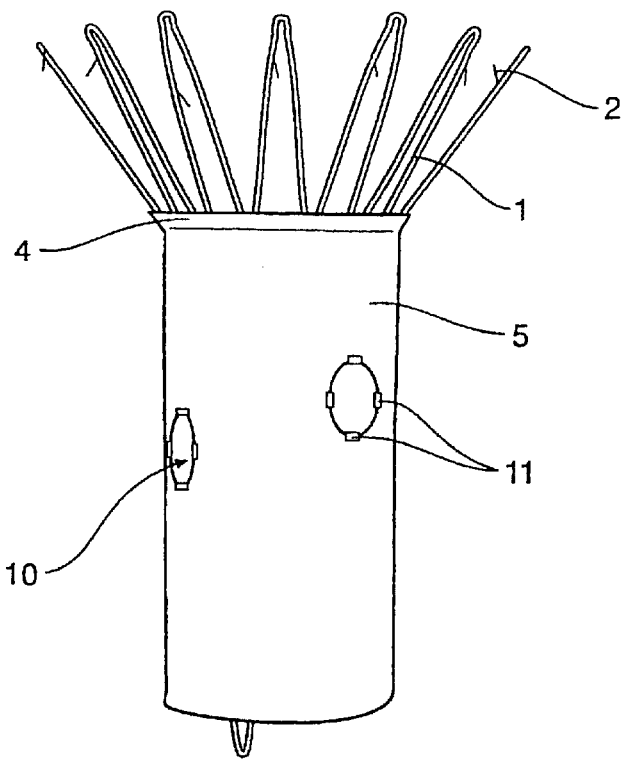
FIG. 1 is an outside view of one embodiment of the present invention illustrating the top stents, bio-compatible material tube with fenestrations and small radiopaque beads and metal loop at the base of the bio-compatible material tube.

DESCRIPTION OF A PREFERRED
EMBODIMENT OF THE INVENTION

The present invention relates generally to the field of the treatment of aortic disease and in particular to endoluminal aortic stents which allow accurate placement of a fenestrated covered stent in the aorta. In particular it is capable of being deployed and positioned accurately above the renal arteries in the treatment of infra-renal aortic aneurysmal disease.

The drawing figures illustrate the basic steps comprising the method as well as illustrating the features of one embodiment of the present invention.

Figure 2:
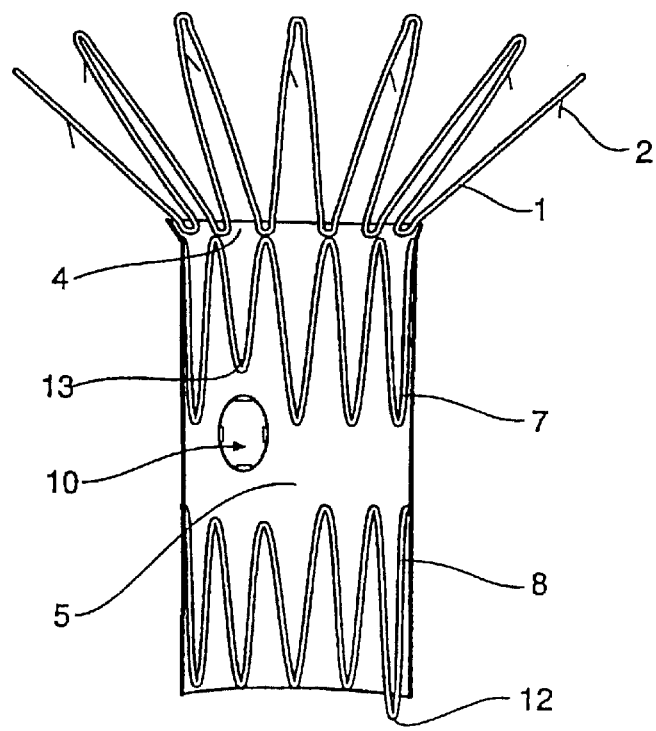
FIG. 2 is an inside view of the embodiment of the present invention illustrating the internal stents and their relationship with the fenestrations for the intersecting arteries.

FIGS. 1 and 2 show an outside view of one embodiment of the present invention. A proximal stainless steel or nitinol stent such is Z stent 1 with caudally facing barbs 2 is stitched to a top ring 4 of a bio-compatible material tube 5. The proximal Z stent 1 extends proximally from the bio-compatible material tube 5. Two further stainless steel or nitinol Z stents 7 and 8 are fitted within the bio-compatible material tube 5. The Z stents are stitched at intervals to the bio-compatible material tube but in part of the bio-compatible material tube stitching is omitted to enable a longitudinal fold to be made in the bio-compatible material tube as will be discussed later. Fenestrations 10 are provided in the bio-compatible material tube 5 providing an aperture in the tube which will in use align with the renal or other arteries. The fenestrations 10 are customized in size and position for the renal arteries following computer tomography and angiography and their peripheral edges are marked with small gold radiopaque beads 11 which help to identify the fenestrations with X-rays. There is a long loop 12 in one of the crowns of the Z stent 8 which extends distally of the bio-compatible material tube 5 and which holds the anterior of the stent within the delivery device as will be discussed later.

As can be particularly seen in FIG. 2, which shows the inside view of the prosthesis, there is a shortened loop 13 of one of the crowns of the top inner Z stent 7 which defines clearance for and permits placement of the fenestrations for the renal arteries at the desired position.

Figure 3:
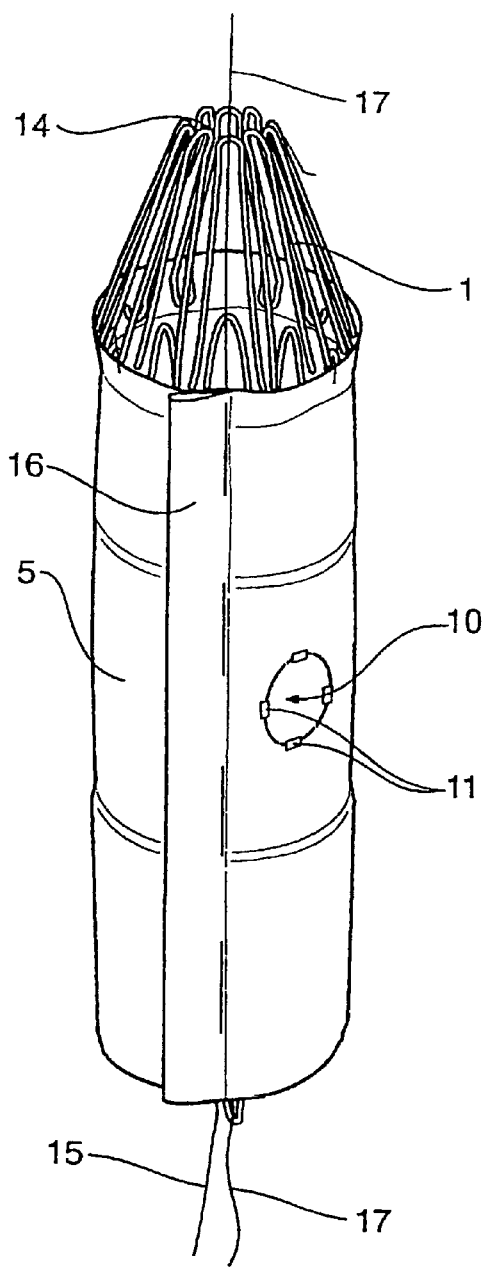
FIG. 3 is an outside perspective view of the embodiment of the present invention illustrating how the material of the bio-compatible material tube may be folded back and held in place by a threaded trigger wire. The stents attached to the inside surface of the material of the bio-compatible material tube are incomplete posteriorly to allow a section of the material of the bio-compatible material tube to be folded and held with a trigger wire threaded through the material.

FIG. 3 is a perspective view of the prosthesis where the proximal crowns 14 of the Z stent 1 have been drawn together manually to facilitate their insertion into a proximal capsule (not shown). A trigger wire 17 is used to retain the crowns within the capsule. The same trigger wire or another trigger wire 15 is also used to retain a longitudinal tuck in the bio-compatible material tube 5 thus narrowing the diameter and leaving a fold 16 of excess material to the side of the prosthesis. The trigger wire 17 also passes through the loop 12 to assist with retaining the distal end of the prosthesis after withdrawal of the sheath as will be discussed later. This enables rotation of the prosthesis within the artery to accurately position it before final release. The trigger wire 15 is inserted through the surface of the DACRON or other material intermittently to create a series of stitches to form the seam-like fold of material 16 as more clearly depicted in FIG. 4.

Figure 4:
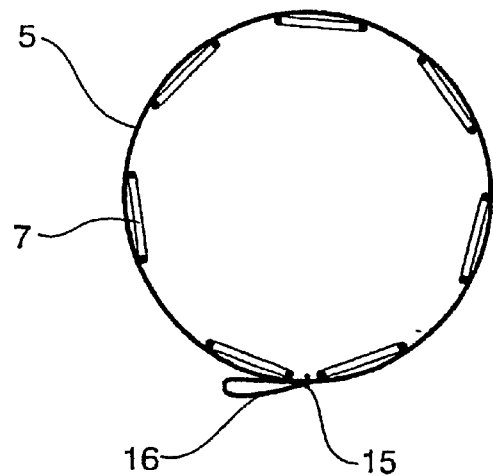
FIG. 4 is a cross-section view of the embodiment of the present invention before release of the trigger wire.

FIG. 4 shows a cross section view of the prosthesis before release of the trigger wire 15 from the fold 16 of material. The seam-like fold 16, held in place by the stitched-on trigger wire 15, provides a diameter which is narrower than the diameter of the aorta thereby enabling the prosthesis to be maneuvered both up and down and rotationally 360 degrees, on release of the present invention from a sheath, and after catheterization as will be discussed in reference to FIG. 8, to ensure accurate placement of the fenestrations in relation to the renal arteries.

Figure 5:
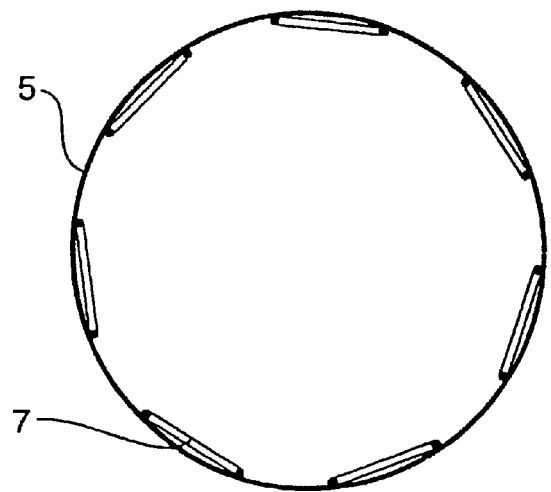
FIG. 5 is a cross-section view of the embodiment of the present invention after release of the trigger wire. The trigger wire has been withdrawn and the folded bio-compatible material unfurled, allowing the stent to expand to its full extent, holding it against the aortic wall with a radial force.

FIG. 5 shows a cross section view of the prosthesis after release of the trigger wire. i.e. in full deployment.

Figure 6:
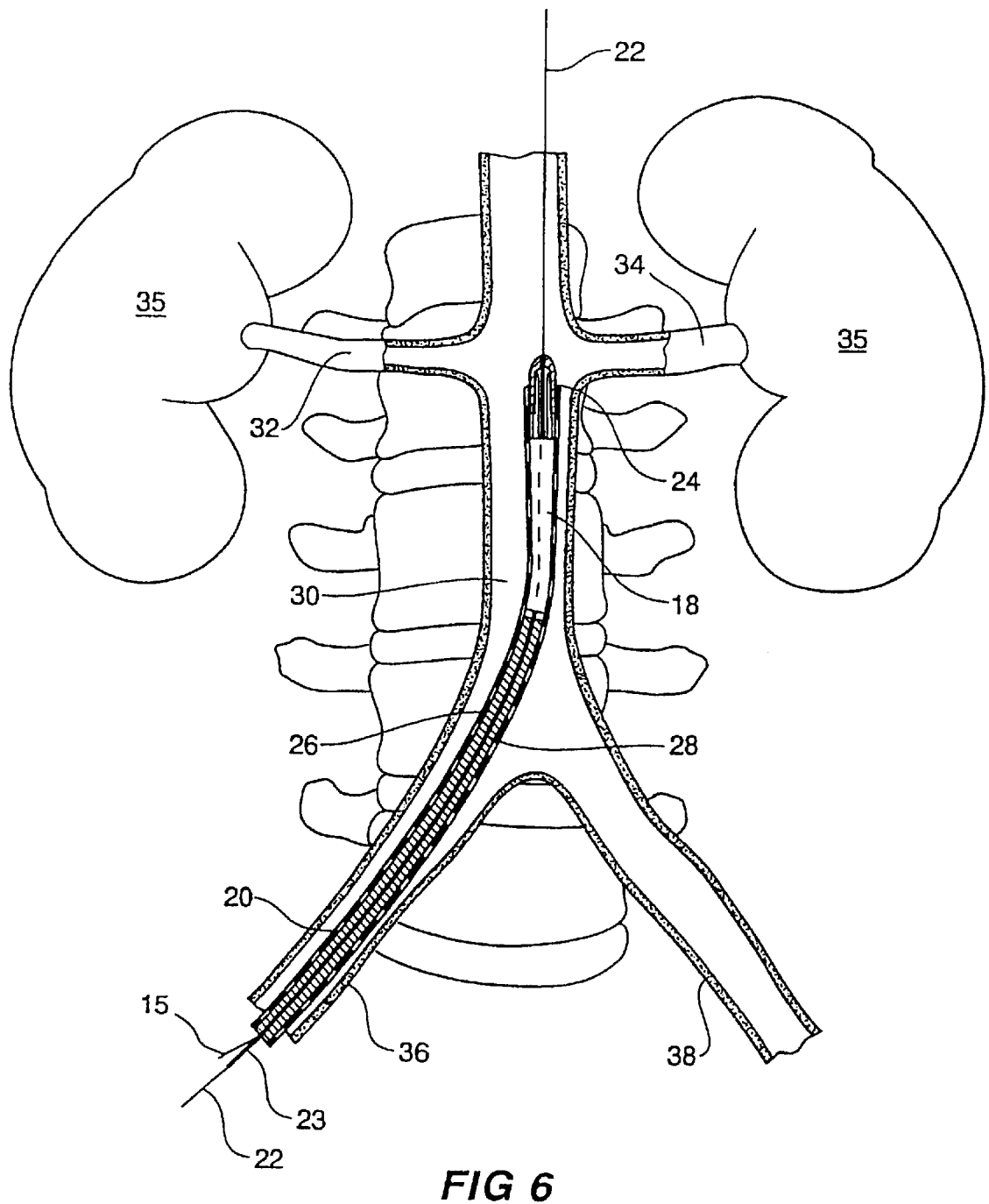
FIG. 6 is a view of the aorta and renal arteries with the prosthesis of this embodiment of the present invention within the delivery device. The top stents of the present invention have been manually pulled together and covered with a top cap whilst the lower part of the present invention sits snugly above the obturator and within the sheath which are all threaded over a guide wire which mounts the present invention to the correct position.

FIG. 6 is a view of the aorta 30, the renal arteries 32 and 34 extending to the kidneys 35 the femoral arteries 36 and 38 and the delivery device which introduces the prosthesis 18 of the present invention to the aorta 30 via a groin incision to one of the femoral arteries 36.

The delivery device generally shown as 20 is inserted over a plastic covered metal guide wire 22 and comprises a stainless steel proximal cap 24 mounted on a flexible steel tube 23. The proximal cap 24 covers the top part of the proximal Z stent and a sheath 26 covering the prosthesis including bio-compatible material tube 5 and the remainder of the Z stents and extends over part of the proximal cap 24 during insertion. The sheath 26 is fitted over a plastic obturator 28 which is sufficiently long to protrude from the femoral artery and groin incision to enable manual movement thereof. The plastic obturator 28 is in a sliding fit on the flexible steel tube 23. The obturator 28 sits snugly under the sheath and holds the prosthesis in position both on insertion and later when the sheath is drawn back over the obturator as depicted in FIG. 7 thereby exposing the fenestrated graft in the semi-deployed position illustrated in FIG. 3.

Figure 7:
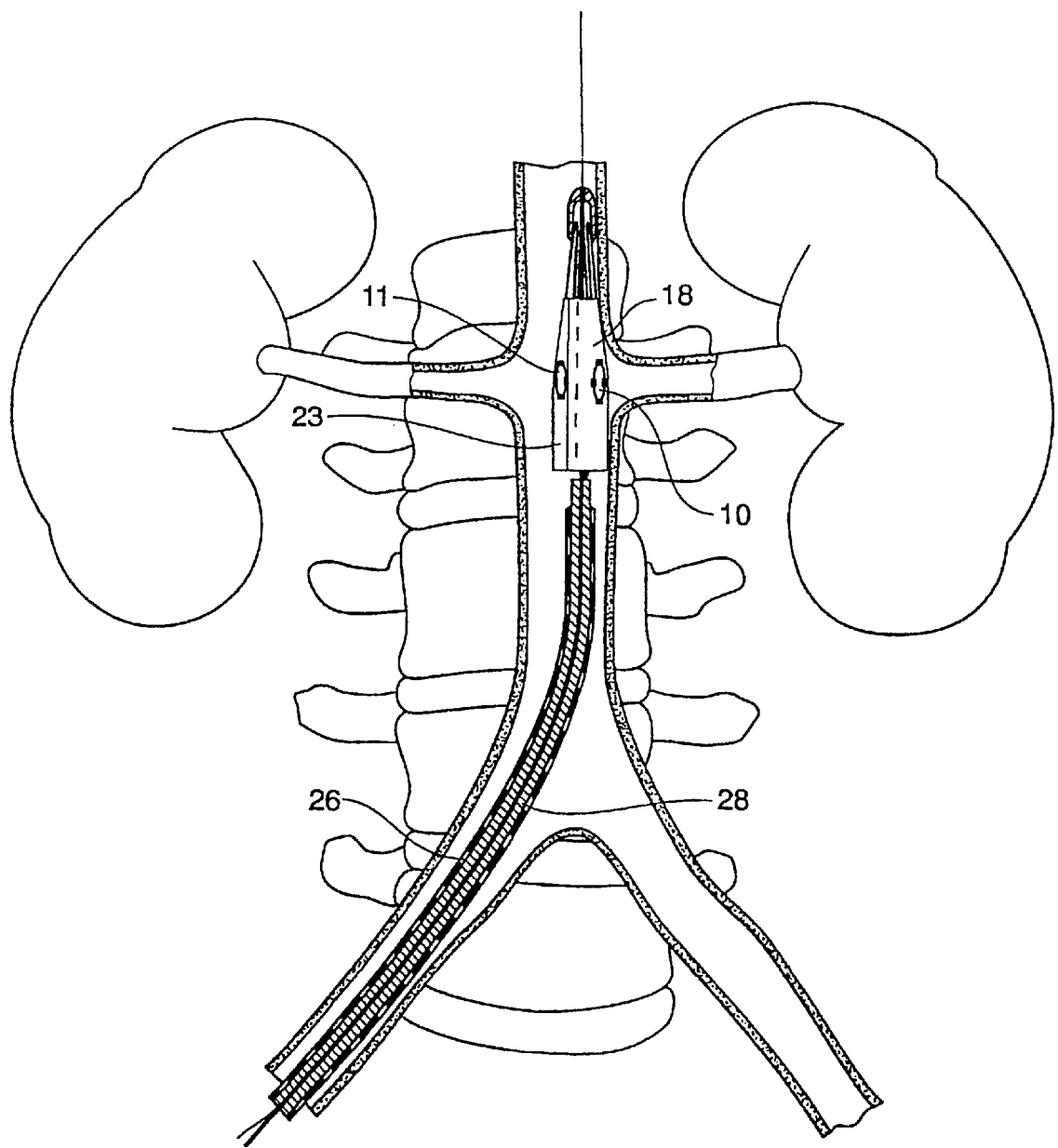
FIG. 7 is a view of the prosthesis of this embodiment of the present invention after its release from the sheath in a semi-deployed position opposite the renal arteries, that is, before release of the trigger wire.

In FIG. 7 the sheath 26 has been withdrawn onto the obturator 28 while leaving the obturator 28 and the proximal capsule 24 in place by preventing relative movement between the flexible steel tube 23 and the obturator 28. The prosthesis 18 is then free to be rotated by movement of the flexible tube 23 and moved longitudinally until the fenestrations 10 are positioned correctly with respect to the renal arteries 32 and 34.

Figure 8:
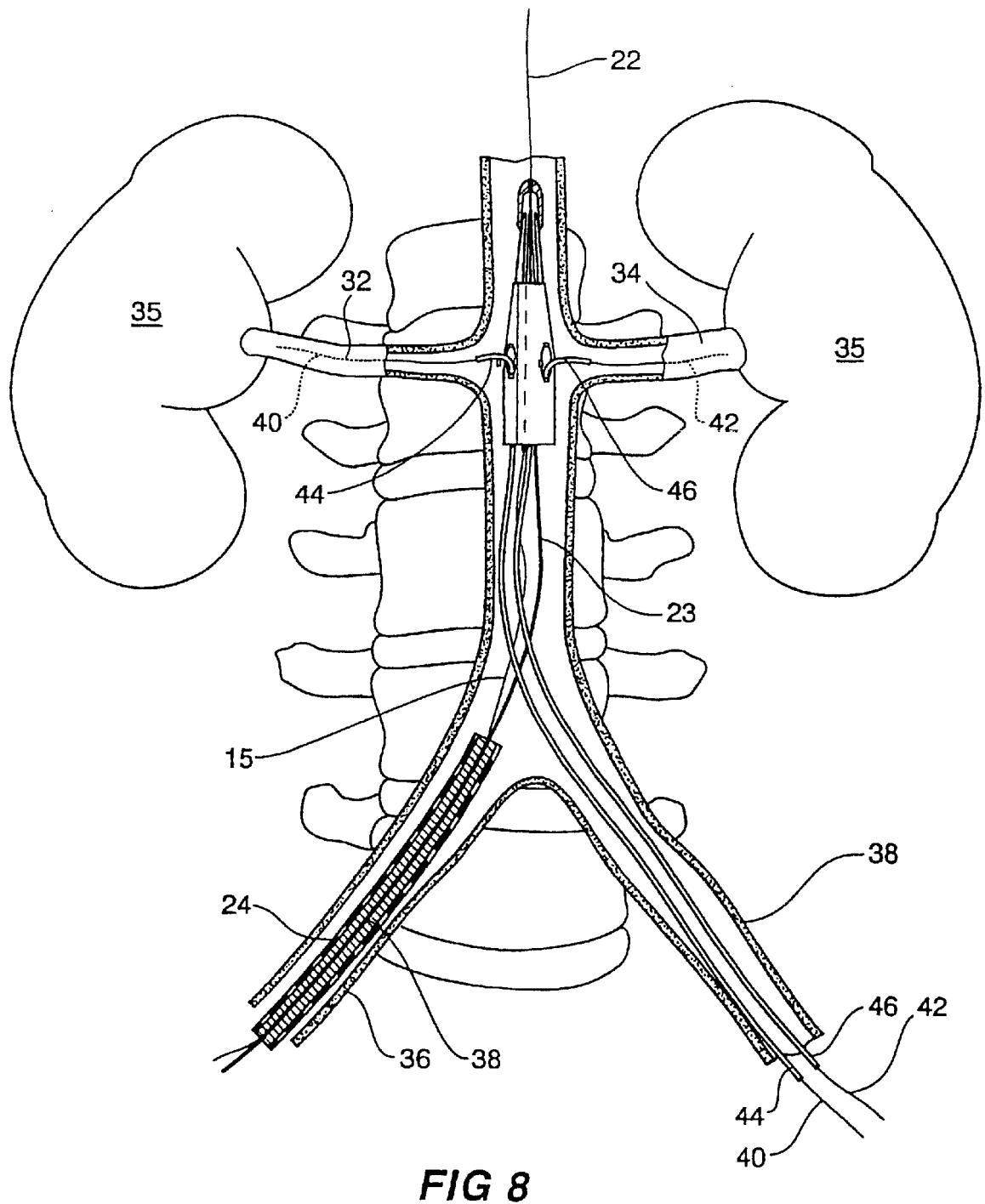
FIG. 8 is a view of the prosthesis of this embodiment of the present invention in a semi-deployed position where the fenestrations of the present invention have been cannulated by a guide wire from the contralateral groin over which two angiography catheters have been passed in order to fix the stent firmly in the correct positions prior to full deployment, that is, prior to release of the trigger wire.

FIG. 8 is a view of the aorta 30, the renal arteries 32 and 34 extending to the kidneys 35 the femoral arteries 36 and 38 and the delivery device 20 where the obturator 28 and sheath 24 have been withdrawn back to one of the femoral arteries 36. This is achieved by holding the flexible steel tube 23 stationary and moving the sheath 26 and obturator 28 relative to it. The trigger wire 15 remains in place. This allows room for the introduction of the guide wires 40 and 42 and angiography catheters 44 and 46 that have been inserted via an incision in the contralateral groin (not shown) and up through the contralateral femoral artery 38 and placed in the renal arteries as directed by the right and left angiography catheters 44 and 46. These angiography catheters 44 and 46 are designed with right and left bended necks respectively so as to guide the wire from the aorta 30 into the appropriate renal artery 32 and 34. The guide wires 40 and 42 and angiography catheters 44 and 46 are inserted into the renal arteries 32 and 34 so as to safely and accurately position the fenestrations 10 of the prosthesis of this embodiment of the present invention.

Figure 9:
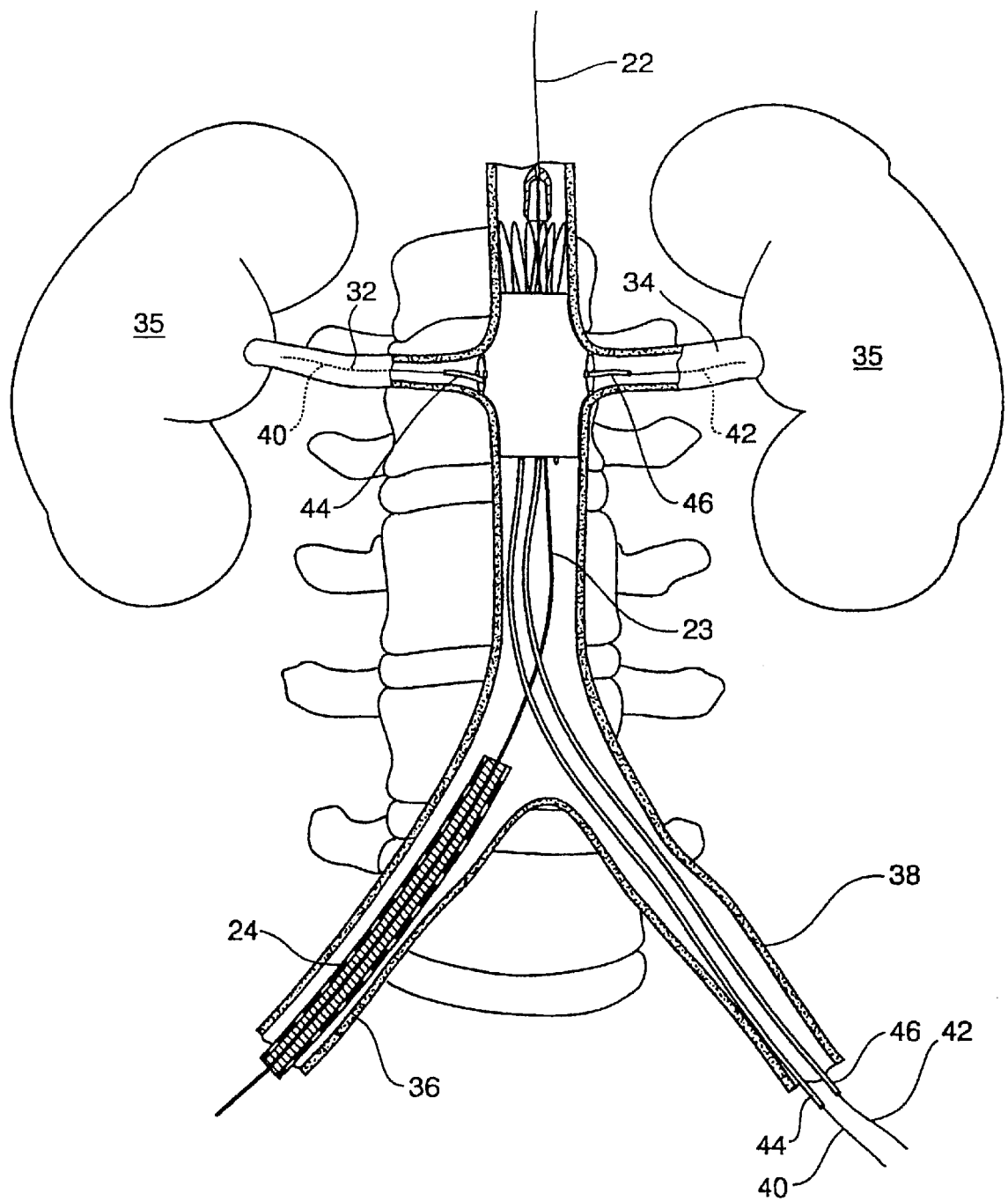
FIG. 9 is a view of the prosthesis of this embodiment of the present invention in full deployment, that is, after release of the trigger wire with the angiography catheters and top cap still in place.

FIG. 9 is a view of the present invention in full deployment after release of the trigger wires 15 and 17 or the single trigger wire carrying out the functions of both trigger wires with the guide wires 40 and 42, angiography catheters 44 and 46 and delivery device 20 still in place. At this stage the proximal Z stent 1 expands out to the wall of the aorta 30 and the barbs 2 engage in to the wall of the aorta to retain the prosthesis 18 in the correct position.

Figure 10:
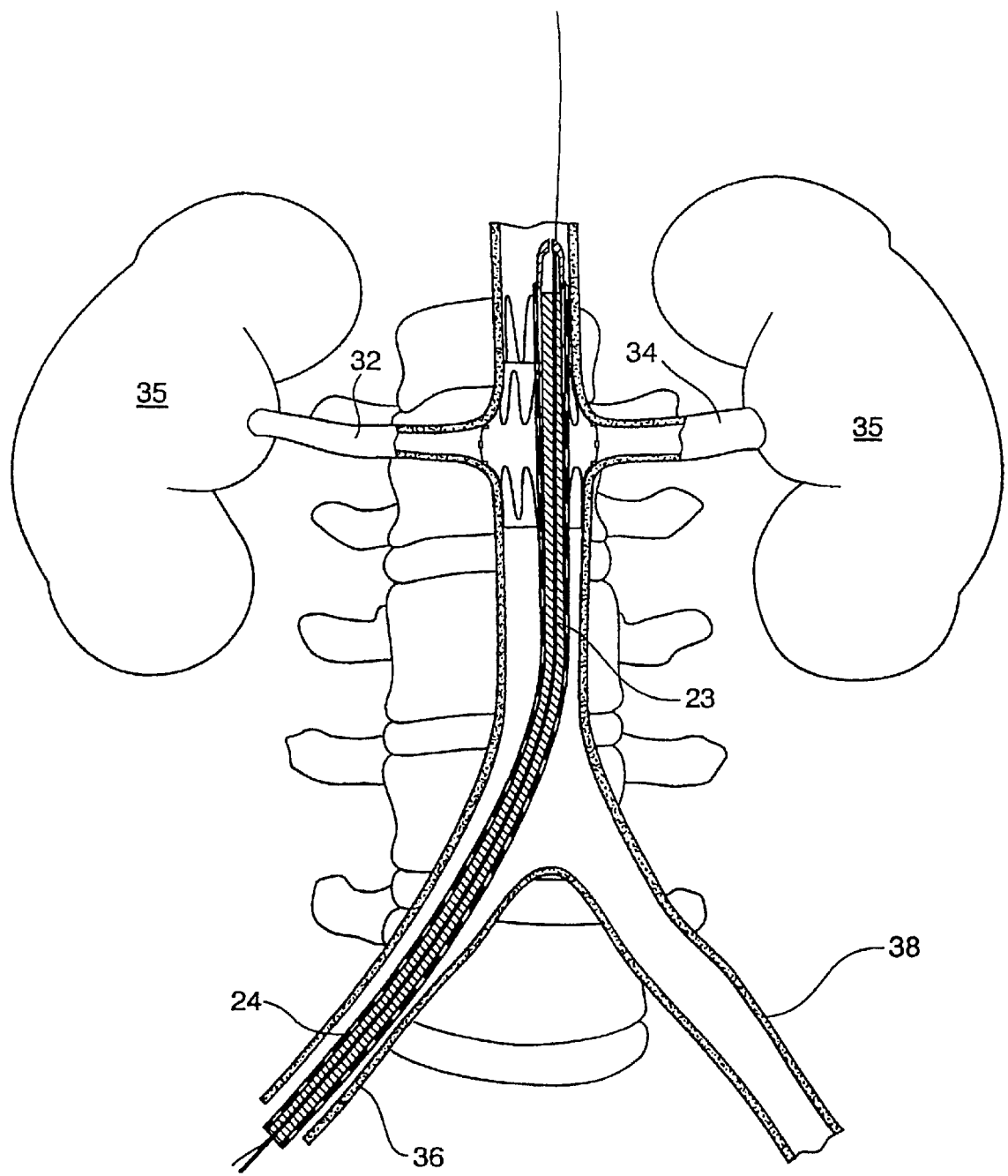
FIG. 10 is a view of the prosthesis of this embodiment of the present invention in full deployment with the angiography catheters and their guide wires withdrawn, and the sheath and obturator of the delivery device pushed up to dock with the top cap in preparation for withdrawal of the delivery device.

In FIG. 10 the angiography catheters 44 and 46 and guide wires 40 and 42 have been withdrawn through the contralateral femoral artery 38, and the obturator 28 and sheath 24 have been pushed up to dock with the proximal capsule 24 in preparation for removal of the complete delivery device 20. This is achieved by holding the flexible steel tube 23 stationery and moving the obturator 28 and sheath 24 relative to it an d towards the proximal capsule.

Figure 11:
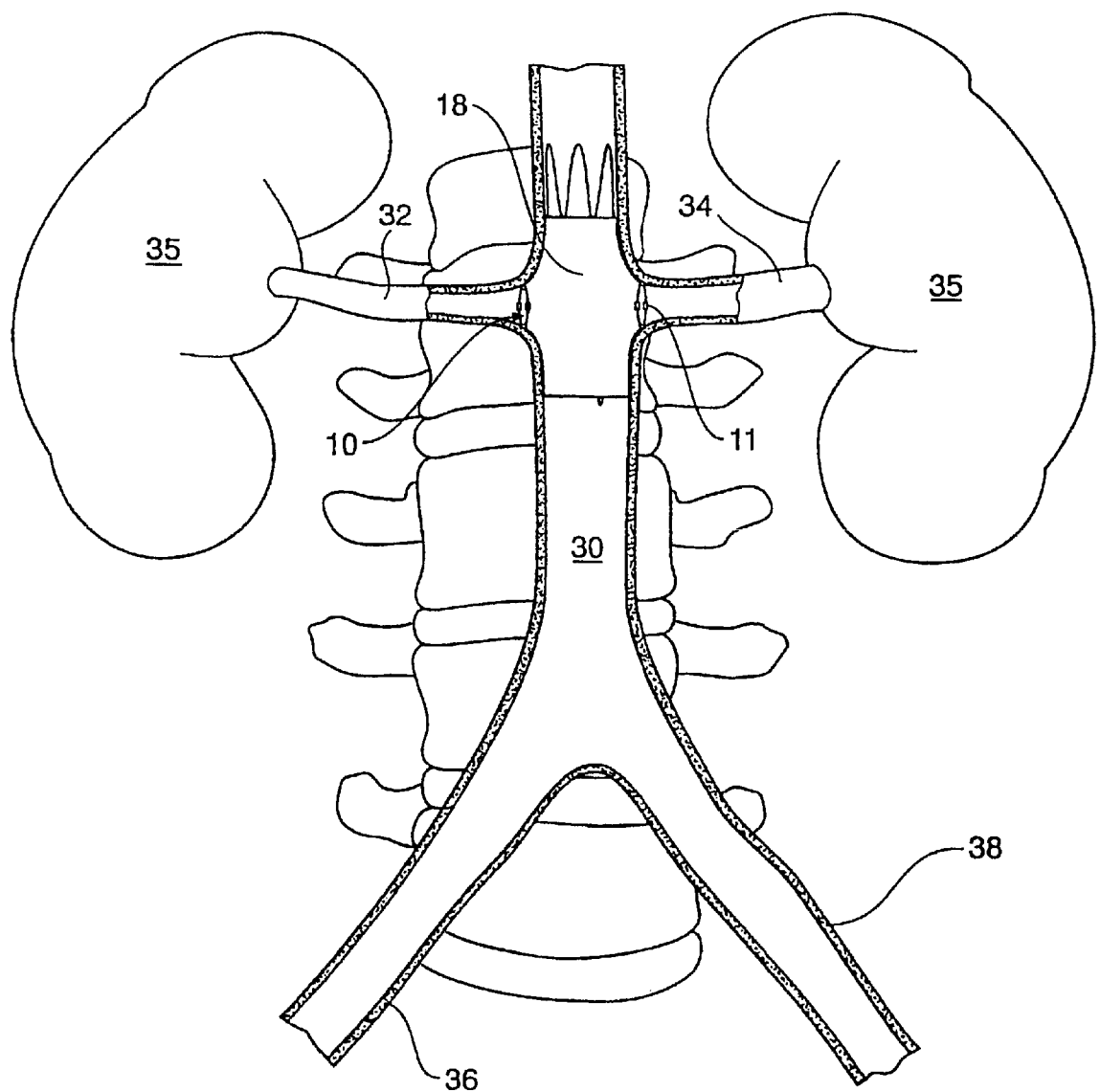
FIG. 11 is a view of the prosthesis of this embodiment of the present invention in full deployment preserving flow to the renal arteries with the sheath, obturator and top cap withdrawn.

FIG. 11 is a view of the prosthesis 18 of the present invention in full deployment, with the delivery device 20 withdrawn, enabling free flow of blood through the aorta 30 and into the renal arteries 32 and 34 via the fenestrations 10.

Post-deployment angiography should be carried out to confirm correct deployment and positioning of the fenestrations.

Modifications which can be made which may be advantageous are as follows.

There may be more than two Z stents attached to, and within, the bio-compatible material tube. More than two Z stents would be used if elongation of the graft of the present invention is required.

The release mechanism may be folded internally either (a) posteriorly or (b) anteriorly and posteriorly with one or two trigger wires respectively.

There may be more than two fenestrations in the bio-compatible material tube where there are more than two intersecting arteries.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A prosthesis comprising two or more stents sutured to a graft of biocompatible material defining a tube, wherein the two or more stents are attached to the inside surface of the tube and at least one fenestration is defined through the tube corresponding to an intersecting artery opening and wherein the two or more stents are positioned proximally and distally adjacent the at least one fenestration and each positioned entirely within the tube.

2. A prosthesis comprising two or more stents sutured to a graft of bio-compatible material defining a tube, wherein the two or more stents are attached to the inside surface of the tube and at least one fenestration is defined through the tube corresponding to an intersecting artery opening.

3. A prosthesis according to claim 2 wherein more than two stents are attached to the tube.

4. A prosthesis according to claim 2 wherein at least one of the stents has caudally facing barbs thereon.

5. A prosthesis according to claim 2 further including a further stent fastened to the tube and extending proximally from the tube.

6. A prosthesis according to claim 5 wherein the further stent has caudally facing barbs thereon.

7. A prosthesis according to claim 2 wherein two or more fenestrations are provided in the tube corresponding to respective intersecting arteries.

8. A prosthesis according to claim 2 wherein the fenestration includes one or more radiopaque markers defining a periphery of the fenestration.

9. A prosthesis according to claim 2 wherein a distal-most one of the stents includes a loop extending distally of the graft material.

10. A prosthesis according to claim 2 further including a release mechanism therefor including one or more trigger wires wherein a portion of the biocompatible material is folded longitudinally with the one or more trigger wires respectively threaded longitudinally through the tube at the fold to retain the prosthesis in a partially compressed state.

11. A method for treating arterial disease at an intersection of two arteries, including the steps of:

X-raying arteries to be treated so as to accurately determine the position of the intersection of the arteries;

providing a prosthesis comprising a selected length of a biocompatible material tube;

forming one or more fenestrations through the tube at locations corresponding to the position of respective arteries at the intersection;

attaching radiopaque markers around the one or more fenestrations; and placing two or more stents into said biocompatible material tube proximally and distally adjacent a fenestration in a manner not covering the fenestration and each of the two or more stents being placed entirely within the tube, thereby providing a customized fenestrated prosthesis to be inserted into an artery to be treated.

12. A method for treating arterial disease at an intersection of two arteries, including the steps of:

X-raying arteries to be treated so as to accurately determine the position of the intersection of the arteries;

providing a prosthesis comprising a selected length of a biocompatible material tube;

forming one or more fenestrations through the tube at locations corresponding to the position of respective arteries at the intersection;

attaching radiopaque markers around the one or more fenestrations; and placing two or more stents into said biocompatible material tube in a manner not covering a fenestration, thereby providing a customized fenestrated prosthesis to be inserted into an artery to be treated.

13. The method as in claim 12 wherein at least one of the stents includes one or more shortened loops to define clearance for a respective fenestration.

14. The method as in claim 11 further comprising the steps of:

manually gathering a top stent, covering the top stent with a top cap and holding the top cap in place with a trigger wire;

stitching a trigger wire through a longitudinal fold in the biocompatible material of the tube to narrow the diameter of the prosthesis;

compressing the prosthesis and placing it into a sheath which fits snugly around the top cap, the tube, the stents and an obturator;

inserting through a femoral artery in a groin the prosthesis using a delivery device that includes the top cap, the sheath, the obturator, and guide wires;

withdrawing the sheath to reveal the prosthesis in semi-deployed position;

positioning the prosthesis;

partially withdrawing the sheath and obturator to enable insertion of angiography catheters and guide wires;

inserting the angiography catheters and guide wires through a contralateral groin into the artery to be treated to provide maneuverability, and accurately positioning the prosthesis by positioning right and left angiography catheters and guide wires through the fenestrations into the intersecting arteries;

releasing the trigger wire to provide full deployment of the prosthesis;

withdrawing the angiography catheters;

pushing the sheath and obturator through the prosthesis to dock with the top cap; and fully withdrawing the delivery device, whereby the fully deployed prosthesis ensures the flow of blood at the intersection of the arteries to be treated.

15. The method as in claim 12 further comprising the steps of:

manually gathering a top stent, covering the top stent with a top cap and holding the top cap in place with a trigger wire;

stitching a trigger wire through a longitudinal fold in the biocompatible material of the tube to narrow the diameter of the prosthesis;

compressing the prosthesis and placing it into a sheath which fits snugly around the top cap, the tube, the stents and an obturator;

inserting through a femoral artery in a groin the prosthesis using a delivery device that includes the top cap, the sheath the obturator and guide wires;

withdrawing the sheath to reveal the prosthesis in semi-deployed position;

positioning the prosthesis;

partially withdrawing the sheath and obturator to enable insertion of angiography catheters and guide wires;

inserting the angiography catheters and guide wires through a contralateral groin into the artery to be treated to provide maneuverability, and accurately positioning the prosthesis by positioning right and left angiograph catheters and guide wires through the fenestrations into the intersecting arteries;

releasing the rigger wire to provide full deployment of the prosthesis;

withdrawing the angiograph catheters;

pushing the sheath and obturator through the prosthesis to dock with the top cap; and fully withdrawing the delivery device, whereby the fully deployed prosthesis ensures the flow of blood at the intersection of the arteries to be treated.

16. The method as in claim 12 wherein more than two stents are attached to the biocompatible material tube.

17. The method as in claim 12 wherein there are more than two fenestrations each of which corresponds to an intersecting artery.

18. A prosthesis comprising two or more stents sutured to a graft of bio-compatible material defining a tube, wherein the two or more stents are attached to the inside surface of the tube and at least one fenestration is defined through the tube corresponding to an intersecting artery opening and wherein said prosthesis further includes a release mechanism therefor including one or more trigger wires wherein a portion of the biocompatible material is folded longitudinally with the one or more trigger wires respectively threaded longitudinally through the tube at the fold to retain the prosthesis in a partially compressed state.

* * * * *